US008031924B2

(12) United States Patent
Can et al.

(10) Patent No.: US 8,031,924 B2
(45) Date of Patent: Oct. 4, 2011

(54) METHODS AND SYSTEMS FOR REMOVING AUTOFLUORESCENCE FROM IMAGES

(75) Inventors: Ali Can, Troy, NY (US); Michael John Gerdes, Albany, NY (US); Harvey Ellis Cline, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 977 days.

(21) Appl. No.: 11/948,205

(22) Filed: Nov. 30, 2007

(65) Prior Publication Data
US 2009/0141959 A1     Jun. 4, 2009

(51) Int. Cl.
G06K 9/00       (2006.01)

(52) U.S. Cl. .................. 382/128; 382/294; 702/19

(58) Field of Classification Search .............. 382/128
See application file for complete search history.

(56) References Cited

U.S. PATENT DOCUMENTS

| | | | |
|---|---|---|---|
| 5,880,473 A | 3/1999 | Ginestet | |
| 6,500,622 B2* | 12/2002 | Bruchez et al. | 435/6 |
| 6,678,398 B2* | 1/2004 | Wolters et al. | 382/128 |
| 6,980,674 B2* | 12/2005 | Anderson et al. | 382/128 |
| 6,990,221 B2* | 1/2006 | Shams | 382/129 |
| 7,187,810 B2* | 3/2007 | Clune et al. | 382/294 |
| 7,219,016 B2* | 5/2007 | Rimm et al. | 702/19 |
| 7,477,931 B2* | 1/2009 | Hoyt | 600/476 |
| 7,668,351 B1* | 2/2010 | Soliz et al. | 382/128 |
| 7,873,407 B2* | 1/2011 | Levenson et al. | 600/476 |
| 2002/0119441 A1* | 8/2002 | Elias | 435/4 |
| 2002/0160443 A1* | 10/2002 | Tsipouras et al. | 435/40.5 |
| 2003/0158470 A1* | 8/2003 | Wolters et al. | 600/317 |
| 2003/0191368 A1* | 10/2003 | Wang et al. | 600/160 |
| 2004/0009098 A1* | 1/2004 | Torre-Bueno | 422/63 |
| 2004/0010192 A1* | 1/2004 | Benaron et al. | 600/431 |
| 2004/0021771 A1* | 2/2004 | Stearns et al. | 348/131 |
| 2004/0225222 A1* | 11/2004 | Zeng et al. | 600/476 |
| 2005/0065440 A1* | 3/2005 | Levenson | 600/476 |
| 2006/0118742 A1* | 6/2006 | Levenson et al. | 250/559.3 |
| 2006/0119865 A1* | 6/2006 | Hoyt et al. | 356/625 |
| 2006/0146346 A1* | 7/2006 | Hoyt | 356/625 |

(Continued)

FOREIGN PATENT DOCUMENTS

| | | |
|---|---|---|
| EP | 1731941 | 12/2006 |
| JP | 80334466 | 12/1996 |

OTHER PUBLICATIONS

Mansfield, James et al., "Autofluorescence Removal, Multiplexing, and Automated Analysis Methods for in-vivo Fluorescence Imaging", Journal of Biomedical Optics, Jul./Aug. 2005, vol. 10(4), 041207-1-041207-9.

(Continued)

*Primary Examiner* — Sath V Perungavoor
(74) *Attorney, Agent, or Firm* — Jenifer E. Haeckl (57) ABSTRACT

Method and systems for removing any inherent autofluorescence associated with a biological material, comprising: acquiring a first reference image of the biological material; acquiring a first set of one or more images of the biological material using one or more filters corresponding to one or more information dyes; applying the one or more additional dyes to the biological material and then acquiring a second set of one or more images comprising a separate image of the biological material with each of the filters corresponding to the information dyes and a second reference image of the biological material; coregistering the first and second reference images; and then removing any inherent autofluorescence exhibited in the informational images acquired.

22 Claims, 3 Drawing Sheets

U.S. PATENT DOCUMENTS

| | | | |
|---|---|---|---|
| 2007/0016078 A1* | 1/2007 | Hoyt et al. | 600/476 |
| 2007/0016082 A1* | 1/2007 | Levenson et al. | 600/476 |
| 2007/0091428 A1* | 4/2007 | Wilson et al. | 359/391 |
| 2008/0015446 A1* | 1/2008 | Mahmood et al. | 600/476 |
| 2008/0032328 A1* | 2/2008 | Cline et al. | 435/40.5 |
| 2008/0212866 A1* | 9/2008 | Lett et al. | 382/133 |
| 2009/0141959 A1* | 6/2009 | Can et al. | 382/133 |
| 2009/0245605 A1* | 10/2009 | Levenson et al. | 382/128 |
| 2009/0245611 A1* | 10/2009 | Can et al. | 382/133 |
| 2010/0121172 A1* | 5/2010 | Ladic et al. | 600/407 |

OTHER PUBLICATIONS

Knight, A. W. et al., "The Application of Fluorescence Polarisation for the Enhanced Detection of Green Fluorescent Protein (GFP) in the Presence of Cellular Auto-Fluorescence and Other Green Fluorescent Compounds", The Royal Society of Chemistry 2000, 125, 499-506.

Steinkamp, John A. et al, "Dual-Laser, Differential Fluorescence Correction Method for Rducing Cellular Background Autofluorescence", Cytometry 7:566-574 (1986).

Niswender, K.D. et al., "Quantitative Imaging of Green Fluorescent Protein in Cultured Cells: Comparison of Microscopic Techniques, Use in Fusion Proteins and Detection Limits", Journal of Microscopy, vol. 180, Pt. 2, Nov. 1995, pp. 109-116.

Pepperkok Rainer et al., "Simultaneous Detection of Multiple Green Fluorescent Proteins in Live Cells by Fluorescence Lifetime Imaging Microscopy", Current Biology 1999, 9:269-272.

Billinton, Nicholas et al., "Seeing the Wood Through the Trees: A Review of Techniques for Distinguishing Green Fluorescent Protein from Endogenous Autofluorescence", Analytial Biochemistry 291, 175-197 (2001).

Schnell, Stephen et al., "Reduction of Lipofuscin-like Autofluorescence in Fluorescently Labeled Tissue", The Journal of Histochemistry & Cytochemistry, vol. 47(6): 719-730, 1999.

Neumann, Michael et al., "Simple Method for Reduction of Autofluorescence in Fluorescence Microscopy", The Journal of Histochemistry & Cytochemistry, vol. 50(3): 437-439, 2002.

PCT/EP2008/066189 Search Report, Feb. 27, 2009.

JP8334466 Abstract, Dec. 17, 1996.

PCT/EP2008/066189 Written Opinion, Jun. 10, 2010.

* cited by examiner

METHODS AND SYSTEMS FOR REMOVING AUTOFLUORESCENCE FROM IMAGES

BACKGROUND

The invention relates generally to methods and systems for removing inherent autofluorescence of biological materials from images of those biological materials.

Tissue auto-fluorescence (AF) is a fundamental problem in microscopy and surgical applications. It reduces the signal detection sensitivity, and in some cases may cause failure in the detection of fluorescent dye signals. Accurate detection of protein-specific fluorescent dyes is critical for many microscopy applications, as such molecular pathology imaging, where quantitation of molecular pathways has significant implications such as predicting drug response, therapy planning, and population segmentation of cancer patients.

In recent years the development of numerous fluorescent dyes has made optical fluorescent microscopy the method of choice for disease recognition. Numerous studies have used fluorescent spectroscopy techniques to study the variations in tissue auto-fluorescence for diagnosis of colorectal, breast, lung, cervical, colon, gastrointestinal tract, and cancer. However, these methods require extensive modeling of tissue-specific auto-fluorescence (AF) spectra. This tedious modeling process, which may not always be sufficient, can be side stepped by using multiplexing techniques in which artificially introduced dyes or dyes are used to track specific proteins. Multiplexing involves acquiring images of different dyes with non-overlapping emission or excitation spectra through filter cubes that match the emission and excitation spectra of each dye. However, in such methods, the protein-specific fluorescence emitted by these dyes, upon appropriate external light excitation, is combined in unknown proportions with the inherent tissue autofluorescence (AF) signal, greatly reducing their efficacy. Thus separation and removal of inherent tissue AF would greatly improve the accuracy of such methods.

Although various strategies for tissue AF removal have been proposed and studied in the literature, such as, using liquid crystal tunable filters, fluorescence polarization, dual-wavelength differential fluorescence correction, confocal laser scanning microscopy and time-resolved fluorescence microscopy, many of these strategies make use of expensive multi-spectral imaging hardware, over the entire spectral range, followed by spectral un-mixing. Apart from hardware augmentation, there are also various chemical processes that can be used to reduce the effect of tissue AF.

Digitally acquired fluorescence microscope images can also be processed retrospectively using software methods, to separate tissue AF from the relevant dye fluorescence. Some of these methods rely on acquiring estimates of the pure AF signal and using them to remove AF from images containing both dye and AF signals by a weighted subtraction. Others use statistical correlation techniques to correct for the additive AF signal. While these techniques are more cost effective than using multi-spectral imaging hardware, they may not be able to completely remove the AF component from fluorescence microscopy images.

BRIEF DESCRIPTION

The methods and systems of the invention generally use a two-step image acquisition process to remove the inherent tissue AF from fluorescent images. These methods and systems may be used with or without chemical and/or photobleaching AF reduction techniques.

Rather than acquiring images of all the dyes all at once using a set of optimum filter cubes tuned to specific dyes, the image acquisition is carried out in two general steps. In the first step, a reference image of the biological material is acquired. The reference image may be acquired by staining the biological material first with a reference dye, such as one or more low AF dyes (e.g. ultra-violet or infra-red), and then a first reference image is acquired using a filter corresponding to the low AF dye. The reference image may also be acquired without applying a reference dye, by using a filter corresponding to a cyan fluorescent protein. A first set of images also comprises images taken with filters corresponding to one or more additional dyes before such dyes are applied. These images taken with the corresponding filters, except the low AF dyes, represent the tissue autofluorescence at their specific spectra. In the second step, the additional dyes are added, and then separate images with each of the filters, including the reference filter, are acquired. The reference images are coregistered by aligning the first reference image with the second reference image using the structures that are common in both steps. Then, a robust estimation process is used to separate the AF signal acquired in the first step from the AF and dye signal acquired in the second step, resulting in images that are free of AF. The methods and systems of the invention have the technical effect of preserving the signal while reducing or eliminating the AF, which increases the resulting signal-to-AF ratio and the overall sensitivity of detection. These cost effective methods and systems obviate the need for complicated and expensive instrumentation or chemical techniques. The methods and systems are adaptable to wide array of tissue micro arrays (TMA). However, they are not limited to use with TMAs and may be applied to any fluorescence imaging application in which a reference low AF dye or probe and an additional dye or fluorescent probe are used for comparison, and successive images using filters corresponding to the reference dye and the active dye can be taken and coregistered. For the purpose of disclosing these methods and systems, the term dye as used herein, encompasses fluorescent and non-fluorescent imaging agents, and is used interchangeably in the examples herein, but are not intended to be limiting in their scope or use.

An embodiment of the method of the invention, for removing any inherent autofluorescence associated with a biological material, generally comprises the steps of: a) acquiring a first reference image of the biological material; b) acquiring a first set of one or more images of the biological material using one or more filters corresponding to one or more information dyes; c) applying the one or more additional dyes to the biological material and then acquiring a second set of one or more images comprising a separate image of the biological material with each of the filters corresponding to the information dyes and a second reference image of the biological material; d) coregistering the first and second reference images; and e) then removing any inherent autofluorescence exhibited in the images acquired in steps c).

The first and second reference images may be acquired using a filter corresponding to a cyan fluorescent protein; and/or wherein step a) further comprises the step of, applying a reference dye, having a high signal to autofluorescence ratio, to the biological material and wherein the first and second reference images are acquired using a filter corresponding to the reference dye. The reference dye may comprise a dye that corresponds to the UV spectrum, such as, but not limited to DAPI, and/or a dye that corresponds to the IR spectrum.

The first reference image may be a fixed image having a coordinate system and second reference image is a moving image having a coordinate system, and wherein the reference images are coregistered at least in part, to form a composite having a coordinate system, by estimating one or more underlying transformation parameters to map the moving image onto the fixed image coordinate system. The reference images may be coregistered, at least in part, using a similarity transform that incorporates translation, rotation, and scaling.

An embodiment of the system of the invention for removing inherent autofluorescence associated with a biological material, generally comprises: a) a processing device adapted to analyze a reference image of a biological material that exhibits the presence of one or more reference dyes, having a high signal to autofluorescence ratio; b) one or more filters corresponding to the reference dye and one or more filters corresponding to one or more information dyes; c) a digital imaging device adapted to acquire a first set of one or more images of the biological material, in conjunction with the filters corresponding to the reference dye and the one or more information dyes; and further adapted to acquire a second set of one or more images of the biological material, wherein the biological material further exhibits the presence of one or more of the information dyes, in conjunction with the filters corresponding to the reference dye and the one or more information dyes; wherein the second set of images comprises a separate image of the biological material with each of the filters corresponding to the reference dye and the one or more information dyes; and wherein the processing device is further adapted to coregister the reference images; and then remove the inherent autofluorescence, from the images exhibiting the presence of one or more of the information dyes. If a reference dye is used, at least one of the reference dyes may correspond to the UV spectrum and/or the IR spectrum.

The digital imaging device may be adapted to acquire a reference image of the biological material using a reference filter corresponding to a cyan fluorescent protein; wherein the processor is adapted to coregister the reference images by estimating one or more underlying transformation parameters to map the image coordinate system. The reference images may be coregistered using, but not necessarily limited to, one or more intensity-based or featured based parameters. The reference images may be coregistered, at least in part, using a similarity transform that incorporates translation, rotation, and scaling.

Another embodiment of the system of the invention for removing inherent autofluorescence associated with a biological material, generally comprises: a) a processing device adapted to analyze a reference image of a biological material taken using a reference filter corresponding to a cyan fluorescent protein, having a high signal to autofluorescence ratio; b) one or more filters corresponding to one or more information dyes; c) a digital imaging device adapted to acquire a first set of one or more images of the biological material, in conjunction with the reference filter and the filters corresponding to the one or more information dyes; and further adapted to acquire a second set of one or more images of the biological material, wherein the biological material further exhibits the presence of one or more of the information dyes, in conjunction with the reference filters and the filters corresponding to the one or more information dyes; wherein the second set of images comprises a separate image of the biological material with the reference filter and with each of the filters corresponding to the one or more information dyes; and wherein the processing device is further adapted to coregister the reference images; and then remove the inherent autofluorescence, from the images exhibiting the presence of one or more of the information dyes. Similarly, the reference images may be coregistered using, but not limited to, an intensity-based or a featured based parameters. The reference images may also be coregistered, at least in part, using a similarity transform that incorporates translation, rotation, and scaling.

DRAWINGS

These and other features, aspects, and advantages of the present invention will become better understood when the following detailed description is read with reference to the accompanying drawings in which like characters represent like parts throughout the drawings, wherein:

FIG. 1 at (a) shows a joint distribution of the first acquisition and the second acquisition intensities calculated using all images on the TMA. The first acquisition comprises the image of the AF, and the second acquisition is after the dye is added. The line shows the estimated initial line.

FIG. 1 at (b) shows a joint distribution of the first acquisition and the second acquisition intensities. The line represents the final fitted line after the algorithm converges.

DETAILED DESCRIPTION

The methods and systems of the invention comprise a two-step image acquisition process to enhance the accuracy of multiplexing and other fluorescent imaging of biological material. In the first step, a reference image of the biological material is acquired. This image may be acquired simply by using a filter corresponding to a cyan fluorescent protein, or, the tissue may be stained first with a dye or fluorescent imaging agent that has the highest signal to autofluorescence ratio (low AF) and then an image of the tissue stained with the low AF dye, otherwise referred to herein as a reference dye, is taken with a filter cube corresponding to the low AF dye. In addition to the image through the filter cube that corresponds to the low AF dye, otherwise referred to herein as a reference image, additional images are taken using filter cubes corresponding to one or more additional dyes or fluorescent imaging agents. These additional dyes, otherwise referred to herein as information dyes, are not limited in type and include any dye or imaging agent capable of illuminating, enhancing or activating any characteristic or feature of a biological tissue. The terms "additional" and "information", in conjunction with the term "dye", are used herein merely to distinguish from the reference dye or dyes that may be used to acquire the reference image.

The reference image or the first set of images need not necessarily be taken in immediate or close temporal or physical proximity to the time and location of the second set of images. Rather these images may be taken and stored for later retrieval or access. However, the first set of images must be configured and stored so that the reference image of the first set of images can be coregistered with the reference image from the second set of images by using the methods and systems herein for estimating one or more underlying transformation parameters to map the image coordinate system.

The reference image may also be an image taken after a photobleaching step. For example, the methods and systems are also contemplated for use in multiplexing applications. In multiplexing applications, a plurality of dyes (typically corresponding to different channels) and the acquisition of the image for each dye (or channel) are applied and taken in successive rounds, in between which, a photobleaching agent is applied to the biological material so that another dye can be subsequently applied in a successive round of dye application and image acquisition. In such applications, an image of the biological material taken after photobleaching, with an appropriate filter, may serve as a reference image. If more than one reference image is acquired in a given multiplexing process, one or more of these reference images may be used in the co-registering step.

After the first set of images is acquired, the tissue is removed from the imaging device, such as, but not limited to, a microscope, and then the information dyes are applied. As noted, these additional dyes are used to elucidate, enhance or modify one or more features or characteristics of the biological material to gather information from or about the biological material. A second set of images using the entire set of filters, both reference filters and filters corresponding to the additional dyes, is acquired again. The two reference images are registered using the common channel (corresponding to the cyan fluorescent protein or low AF reference dye) between the two steps by estimating one or more underlying transformation parameters to map the composite moving image onto the composite fixed image coordinate system. The AF of the biological material is then removed from the image.

These methods and systems may be used to image and analyze a biological sample to discern inter alia the presence, absence, concentration, and/or spatial distribution of one or more biological materials or targets in a biological sample or tissue.

To more clearly and concisely describe and point out the subject matter of the claimed invention, the following definitions are provided for specific terms, which are used in the following description and the appended claims.

As used herein, the term "biological material" refers to material obtained from, or located in, a biological subject, including sample of biological tissue or fluid origin obtained in vivo or in vitro and biological materials that may be located in situ. Such samples can be, but are not limited to, body fluid (e.g., blood, blood plasma, serum, or urine), organs, tissues, fractions, and cells isolated from, or located in, mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

A biological material may include any material regardless of its physical condition, such as, but not limited to, being frozen or stained or otherwise treated. In some embodiments, a biological material may include a tissue sample, a whole cell, a cell constituent, a cytospin, or a cell smear. In some embodiments, a biological material may include a tissue sample. In other embodiments, a biological material may be an in situ tissue target, if successive images of the targeted tissue can be obtained, first with the reference dye and subsequently with the additional dyes. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseases tissue samples (e.g., tissue section from colon, breast tissue, prostate). A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels.

As used herein, the term "fluorescent imaging agent" refers fluorophores that are chemical compounds, which when excited by exposure to a particular wavelength of light, emit light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS),4-amino-N-[3-vinylsulfonyl)phenyl]naphthalimide-3,5 disulfonate (Lucifer Yellow VS), N-(4-anilino-1-naphthyl) maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron™ Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes, and squaraines.

For applications that additionally use probes, as used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker, which may include a cleavage site) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator.

For applications that require fixing a biological material on a solid support, as used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube. In those embodiments, in which a biological material is adhered to a membrane, the membrane material may be selected from, but is not limited to, nylon, nitrocellulose, and polyvinylidene difluoride. In some embodiments, the solid support may comprise a plastic surface selected from polystyrene, polycarbonate, and polypropylene.

The methods and systems may be adapted for, but are not limited to, use in analytical, diagnostic, or prognostic applications such as analyte detection, histochemistry, immunohistochemistry, or immunofluorescence. In some embodiments, the methods and systems may be particularly applicable in histochemistry, immunostaining, immunohistochemistry, immunoassays, or immunofluorescence applications. In some embodiments, the methods and systems may be particularly applicable in immunoblotting techniques, for example, western blots or immunoassays such as enzyme-linked immunosorbent assays (ELISA).

Image Acquisition Example

This example, although not limiting, acquires images of biological material stained with DAPI, Cy3, and Cy5. Among these three dyes, DAPI, a nuclear marker, is known to have very high signal to autofluorescence ratio (low AF). In the first step, an image of the material using a filter cube corresponding to DAPI is acquired. Additionally, a first set of images of the material using filter cubes corresponding to Cy3 and Cy5 is also acquired. These additional images using filter cubes images corresponding to the additional dyes, before the additional dyes are applied, serve as reference or control images to the images taken after the additional dyes are applied which will then exhibit the autofluorescence corresponding to the additional dyes. Furthermore, an additional, optional image using a filter cube that has minimal cross talk with the DAPI, Cy3, and Cy5 is also acquired. This minimal cross talk filter cube corresponds to a cyan fluorescent protein (CFP). This filter cube is used when acquiring the image of the autofluorescence only, and is used only for image registration, as described further below.

After the first set of images is acquired, the additional dyes are applied to the tissue. Then a second set of images using all of the filter cubes (DAPI, CFP, Cy3, and Cy5) are acquired. Note that the DAPI and CFP images in both acquisitions are essentially the same, and can be used to determine the transformation, described below, that aligns the two sets of images. Once the images are registered, using the steps described below, the autofluorescent images acquired through the Cy3 and Cy5 cubes in the first step are removed from the registered Cy3 and Cy5 images in the second step.

Image registration algorithms are generally grouped into two categories: intensity-based and featured based. Feature extraction based algorithms typically require an initial image analysis and segmentation step. For pathology images, for example, the location, size, and shape of the nuclei can be extracted from DAPI stained images. This information can then be used to align the images using a point matching technique. Features from epithelial tissue, stromal tissue, and glands/background can be extracted from the auto-florescence images as well, however it is generally more challenging to detect feature points consistently in these images.

In this example embodiment, an intensity based registration method is used that does not require any prior segmentation information, and is applicable to a broad class of dyes.

The DAPI image and the tissue AF image, acquired using a CFP filter cube, are added to form a composite image of the first set of images, which is referred to as the fixed image. While the AF image provides large-scale/global information, which is critical for the convergence of the registration algorithms, the DAPI image provides fine structures essential for the accuracy of the registration. The fixed image is denoted by $I_F(x_F, y_F)$. The fixed image is used to define the reference coordinate system of the composite image from the first acquisition. The moving image is denoted by $I_M(x_M, y_M)$, which is the composite image of the second set of images.

Registration is the estimation of the underlying transformation parameters that map the moving image onto the fixed image coordinate system, obtained as arguments that minimize a cost function F;

$$\underset{\theta}{\operatorname{argmin}} F(I_F(x_F, y_F), I_M(T(x_M, y_M; \theta))), \quad (1)$$

where, T represents spatial transformation with parameters θ. More specifically, a similarity transform is used in this embodiment that incorporates translation, rotation, and scaling. The translation and rotation try to correct the misplacement of the tissue slide, and scaling can handle distortions due to small focal plane changes. This transformation maps the moving image into the fixed image coordinate system;

$$T(x_M, y_M; \theta) \equiv \begin{bmatrix} \theta_1 & \theta_2 \\ -\theta_2 & \theta_1 \end{bmatrix} \begin{pmatrix} x_M \\ y_M \end{pmatrix} + \begin{pmatrix} \theta_3 \\ \theta_4 \end{pmatrix}. \qquad (2)$$

Note that higher order transformation models, such as affine or higher order polynomial transformations, can be used if geometric lens distortion is a factor.

There are a great number of measures that can be used as the cost function F, such as, but not limited to, mean-square-error, cross correlation, Kullback-Liebler distance, gradient difference metric, and mutual information. Due to its demonstrated robustness in multi-modality image registration, the negative of mutual information (MI), is used in this example as the cost function. MI is defined as;

$$F(I_F(x_F, y_F), I_M(T(x_M, y_M; \theta))) = \qquad (3)$$
$$-H(I_F(x_F, y_F)) - H(I_M(T(x_M, y_M; \theta)))$$
$$+H(I_F(x_F, y_F), I_M(T(x_M, y_M; \theta)))$$

where H represents the entropy of the image. Here MI is negated to facilitate the minimization process defined in the first equation.

After the first set of images, referred to in this example embodiment as the fixed image, is registered with the second set of images, referred to in this example embodiment as the moving image, the inherent tissue autofluorescence is removed. In this example, the imaging process is modeled and a robust estimation method is used to estimate the model parameters.

As noted, the two-step acquisition provides two images: one AF only image, and one AF plus dye signal image. In this example, a robust regression method is used to compute the Dye Signal image. The image of the AF acquired in the first step is denoted as F(x,y), and the second acquired image (Signal plus AF) is denoted as S(x,y). These two images are related by the following relation, $$S(x, y) = \begin{cases} D(x, y) + \alpha F(x, y) + \beta & \text{if there is dye staining at}(x, y) \\ \alpha F(x, y) + \beta & \text{otherwise,} \end{cases} \qquad (4)$$

where D(x,y) is the unknown dye image, α is the relative gain constant, and β is the relative offset. If the images are normalized to subtract the dark current, β can be set to zero. If the exposure times are known and the excitation light intensity has not changed between the two acquisitions, α can be set to the ratio of the exposure times between the two acquisitions. Note that due to spectral leakage and reflections in the optical system, the observed images typically have an offset component that is a function of the exposure time. Since the exposure times between the first acquisition and the second acquisition are usually different, the relative offset may be modeled as a separate term, rather than incorporating with the unknown term D(x,y). By explicitly parametrizing the relative offset term, the non-negativity constraint on D(x,y) can be imposed, and the cost function adapted accordingly.

Figure 1:
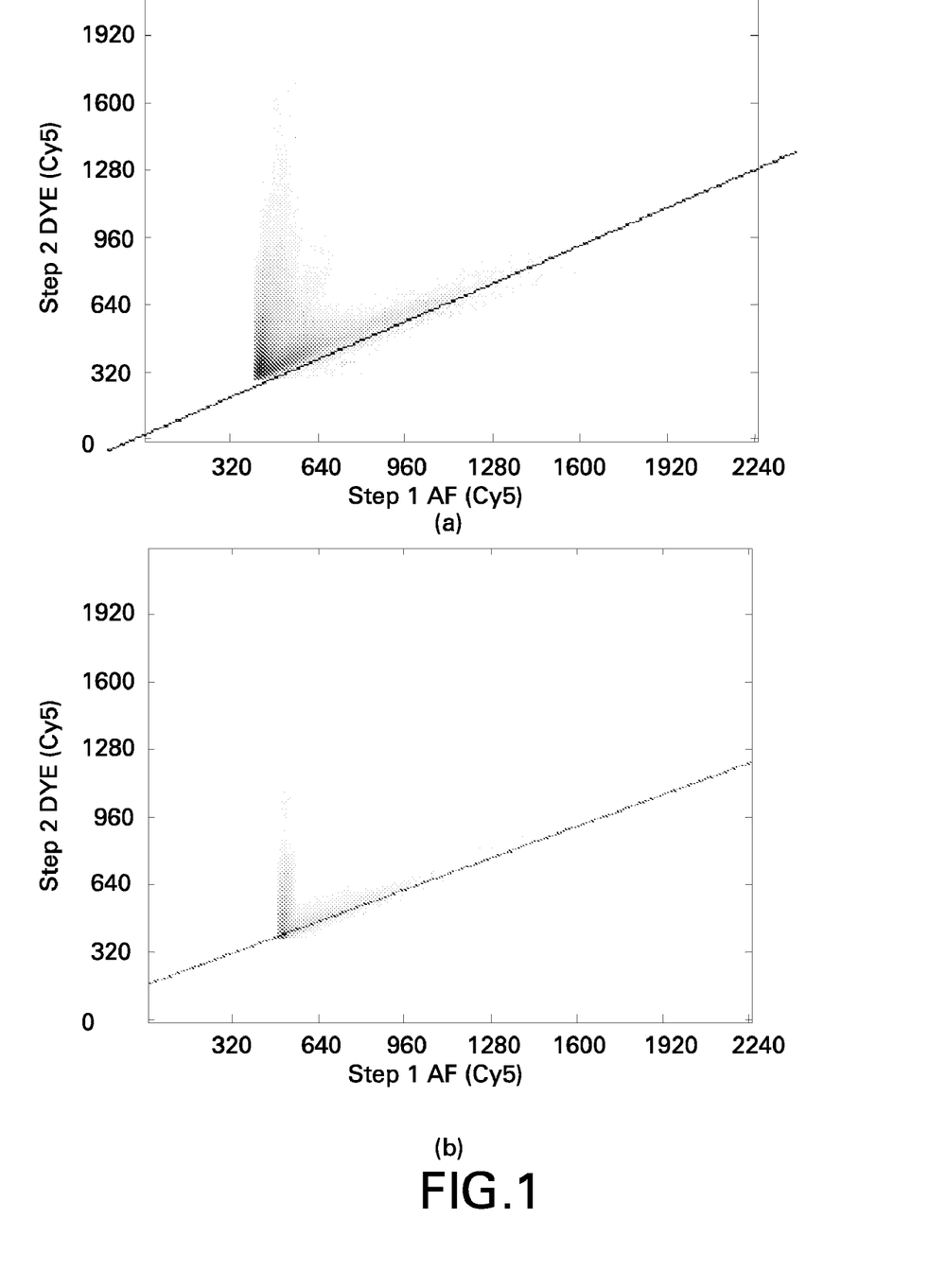

Although various source separation methods are known, such as Statistical decorrelation, Principal Component Analysis, Independent Component Analysis (ICA), and non-negative ICA, all of these methods estimate a coordinate transformation matrix which transforms F(x,y) and S(x,y) into a new coordinate system such that they are as much uncorrelated as possible (PCA), or as independent as possible (ICA). However a close look at the joint distributions of F(x,y) and S(x,y) show that there is no such transform that can achieve fully uncorrelated or independent components. For example, FIG. 1a shows the joint distribution computed from multiple images on the same TMA. The area above the line indicates the expression and the line itself indicates the autofluorescence. Note that the distribution is formed by two clusters; one cluster corresponding to pixels are AF on both images, and the cluster that is a signal image on one image and AF on the other image. Since these two clusters are not orthogonal, and their proportion with respect to each other can significantly change from tissue to tissue, PCA and ICA type methods are generally insufficient. A method that does not require the transformation to be orthogonal is the Non-negative Matrix Factorization (NMF). However this method is generally prone to local minima, and good performance can usually only be achieved with overconstraint systems. Instead, the preferred methods and systems of the invention use a robust regression method to solve the unknown transformation parameters (α,β), and the unknown signal (D(x, y)).

The unknown constants are estimated by treating the D(x, y) as outliers and solving the following robust cost function $$(\hat{\alpha}, \hat{\beta}) = \operatorname*{argmin}_{\alpha,\beta} \sum_{x,y} \rho(S(x, y) - \alpha F(x, y) - \beta), \qquad (5)$$

where ρ is a Huber's robust cost function [34, 35], defined as, $$\rho(r) = \begin{cases} r^2/2 & r \le k \\ kr - k^2r/2 & r > k. \end{cases} \qquad (6)$$

Note that ρ is slightly different than traditional symmetric Huber cost function [34]. It is a simple least squares cost function for r≦k, rather than for r≦|k|. Since D(x,y) is a non-negative function, there are no negative outliers that are significantly smaller than the expected linear form. This one sided non-symmetric cost function adds more cost for negative D(x,y), and it is essential for the convergence of the algorithm by biasing towards the desired solution. Equation 6 can be solved by iterative weighted least squares (IRLS), $$(\hat{\alpha}, \hat{\beta}) = \operatorname*{argmin}_{\alpha,\beta} \sum_{x,y} w(x, y)(S(x, y) - \alpha F(x, y) - \beta)^2 \qquad (7)$$
$$= \operatorname*{argmin}_{\alpha,\beta} (\vec{S} - (\vec{F}, \vec{1})(\alpha, \beta)^T) W (\vec{S} - (\vec{F}, \vec{1})(\alpha, \beta)^T)^T$$

where, $$w(r) = \frac{\rho(r)}{r} = \begin{cases} 1 & r \le k \\ k/r & r > k. \end{cases} \qquad (8)$$

The IRLS solution can then be implemented by iterating the following equations, $$(\hat{\alpha}_k, \hat{\beta}_k)^T = ((\vec{F}, \vec{1})^T W_{k-1}(\vec{F}, \vec{1}))^{-1}(\vec{F}, \vec{1})^T W_{k-1}\vec{S} \quad (9)$$

where $$W_{k-1} = \text{diag}(w(S(x,y) - \hat{\alpha}F(x,y) - \hat{\beta}_{k-1})). \quad (10)$$

FIG. 1a shows S(x,y) versus F(x,y) for all the images on the same TMA. Notice that the joint distribution is composed of two clusters, one formed by corresponding AF on both images, and one formed by AF and Dye Signal. The line shown in FIG. 1a shows the initial estimate for $(\alpha, \beta)$, estimated by fitting a line to the lower bound of the joint distribution. Let $(f_i, s_i)$ are the intensity values on the first and second images such that for all $f_i = F(x,y)$, $$s_i = \min_{(x',y') \in \{(x,y): (f_i - R) < F(x,y) \le (f_i + R)\}} S(x', y') \quad (11)$$

where R is set to (Dynamic Range)/256. The initial parameter values can then be estimated by least squares regression by minimizing;

$$(\hat{\alpha}_0, \hat{\beta}_0) = \underset{\alpha, \beta}{\arg\min} \sum_i (s_i - \alpha f_i - \beta)^2. \quad (12)$$

The scale factor, k in Equations 6&8, is estimated by first determining the local standard deviations by Median Absolute Deviation (MAD);

$$k_i = 1.345 \underset{(x',y') \in \{(x,y):(f_i-R)<F(x,y)\le(f_i+R)\}}{\text{median}}$$
$$\left| S(x', y') - \underset{(x',y')}{\text{median}}(S(x', y') - \hat{\alpha}_0 f_i - \hat{\beta}_0) \right|, \quad (13)$$

and then taking the median of all the local MAD estimates, $$\hat{k} = \text{median}(k_i). \quad (14)$$

Both of the above equations are well known to be robust to outliers.

FIG. 1a shows the joint distribution of F(x,y) and S(x,y) computed from all images on the same TMA. The line on FIG. 1a shows the initial model parameters computed by using Equation 12. Beginning with the initial parameter values, equations 9&10 refine the parameter estimates for each individual image on the TMA. This refinement is capable of handling slight tissue and AF variations among different tissues, particularly normal versus metastasis, or expressed versus non-expressed markers. FIG. 1b shows the joint distribution and the final linear parameters for the image show in FIG. 2 (Right column).

EXAMPLE

Figure 2:
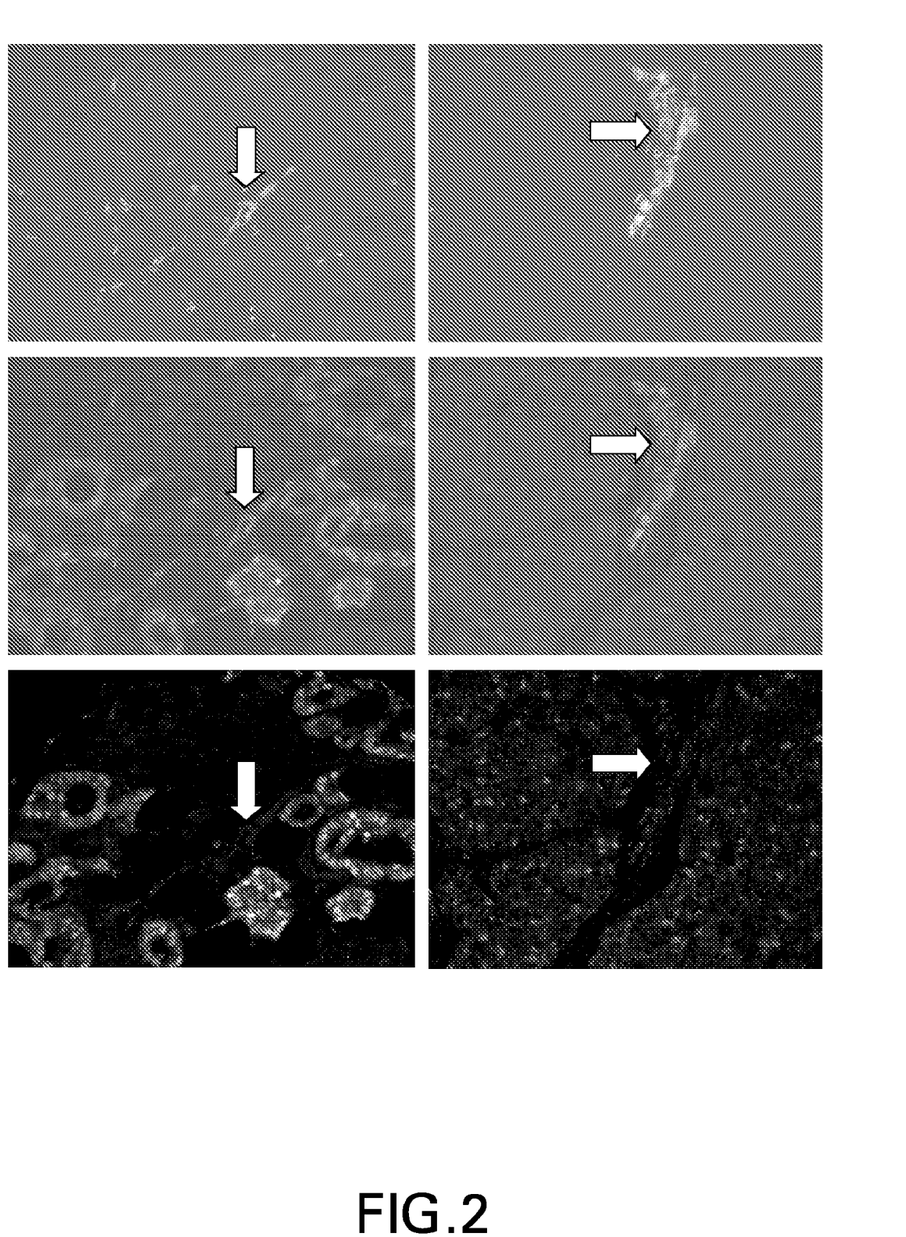
FIG. 2 shows six images of the first and second image acquisitions using various dyes. The top row comprises images from the first image acquisition. The middle row comprises images from the second image acquisition. The bottom row comprises images that are corrected and AF-free. The images in the left column comprise Cy5 dye directly conjugated to Pan-Cadherin, a membrane protein. The images in the right column comprise Cy3 dye directly conjugated to Estrogen Receptor. The arrows indicate tissue regions in the image, such as blood cells and fat, which generally exhibit high AF, in which the AF has been removed.

In this example, TMAs of breast tissue were stained with DAPI, Cy3, and Cy5. DAPI is a nuclear marker that binds to DNA. DAPI was used in this example, for image registration and to quantify percentage expression of nuclear related proteins. Cy3 is directly conjugated with anti-pan-cadherin antibody, a membrane protein, and Cy5 is directly conjugated with anti-Estrogen Receptor (ER) antibody. ER may or may not be expressed depending on if the patient is ER+ or ER−. In this example, expression of ER correlates with response to anti-estrogen treatment (tamoxifen or others) or chemotherapy, and is associated with better-differentiated tumors. In this example, the ER expression is differentiated from AF, particularly from blood cells and fat that shows up as bright structures, because ER expression may be readily confused with real expression. FIG. 2 (Right Column) shows the images of Cy5 channel at the first step (Top), at the second step (Middle), and the corrected image (Bottom). The arrows show the region with high AF, which may be due to bloods cells or fat. The AF is removed while preserving the ER expression. FIG. 2 (Left Column) shows the images of the Cy3 channel. The arrows show the cleaned high AF structures. In addition to removing high-AF structures, low-AF structures are reduced as well.

The methods preserve the signal while reducing the AF; hence the signal-to-AF ratio is increased. High-AF structures such as fat and blood cells are also successfully removed, which is critical to differentiate specific protein expression from non-specific expression. Removing these structures also enables accurate automated protein expression.

The automated system 10 (FIG. 3) for carrying out the methods generally comprises: a storage device 12 for at least temporarily storing one or more images of one or more biological materials; and a processor 14 adapted to analyze a reference image of a biological material that exhibits the presence of a cyan fluorescent protein and/or one or more reference dyes, having a high signal to autofluorescence ratio; one or more filters corresponding to the cyan fluorescent protein and/or reference dyes and one or more filters corresponding to one or more additional dyes; and a digital imaging device adapted to acquire the first set of one or more images of the biological material, in conjunction with the reference filters and the filters corresponding to the one or more additional dyes; and further adapted to acquire a second set of one or more images of the biological material, wherein the biological material further exhibits the presence of one or more of the additional dye, in conjunction with the reference filters and the filters corresponding to the one or more additional dyes; wherein the second set of images comprises a separate image of the biological material with each of the reference filters and the filters corresponding to the additional dyes.

Figure 3:
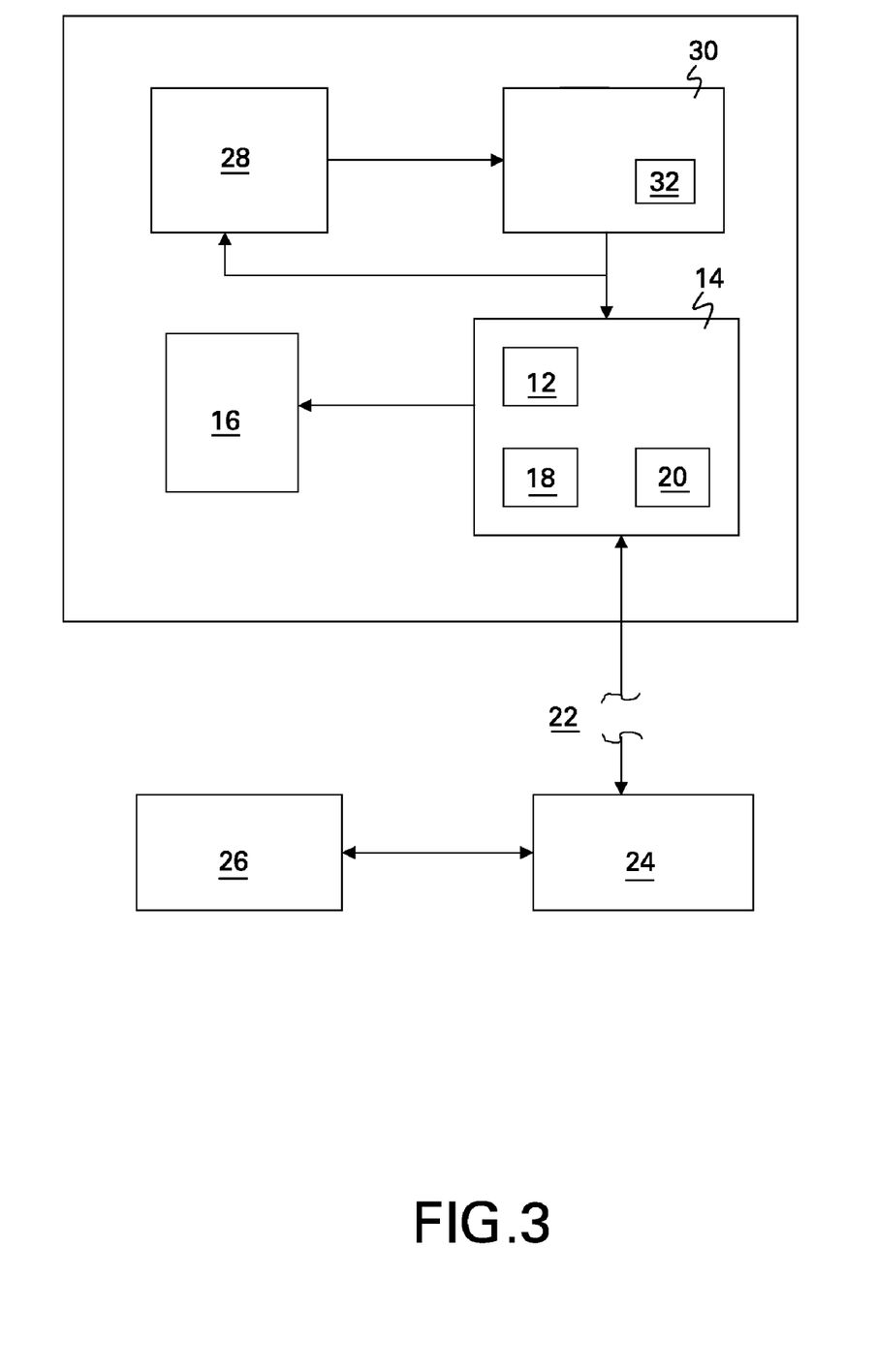
FIG. 3 is a schematic diagram of an embodiment of the automated system for carrying out the methods.

Processing device 14 is further adapted to coregister the reference image; and then remove the autofluorescence, associated with the reference images, from one or more of the images.

The storage device may comprise, but is not necessarily limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the processor or the means for displaying the images, and yet still be accessed through any suitable connection device or communications network including but not limited to local area networks, cable networks, satellite networks, and the Internet, regardless whether hard wired or wireless. The processor or CPU may comprise a microprocessor, microcontroller and a digital signal processor (DSP).

The storage device 12 and processor 14 may be incorporated as components of an analytical device such as an automated high-throughput system that stains and images the TMAs in one system and still further analyzes the images for any number of applications such as, but not limited to, diagnostic applications. One of more of these steps may be configured into one system or embodied in one or more stand-alone systems. System 10 may further comprise a means for displaying 16 one or more of the images; an interactive viewer 18; a virtual microscope 20; and/or a means for transmitting 22 one or more of the images or any related data or analytical information over a communications network 24 to one or more remote locations 26.

The means for displaying 16 may comprise any suitable device capable of displaying a digital image such as, but not limited to, devices that incorporate an LCD or CRT. The means for transmitting 22 may comprise any suitable means for transmitting digital information over a communications network including but not limited to hardwired or wireless digital communications systems. The system may further comprise an automated device 28 for applying one or more of the stains and a digital imaging device 30 such as, but not limited to, an imaging microscope comprising an excitation source 32 and capable of capturing digital images of the TMAs. Such imaging devices are preferably capable of auto focusing and then maintaining and tracking the focus feature as needed throughout processing.

These methods and systems are not limited to any specific imaging agents, morphological dyes, biomarkers or probes. Any fluorescent or nonfluorescent dye or imaging agent that enables some informative aspect or feature of a biological material to be actually or artificially visualized so that it can be digitally imaged and processed, would be suitable. Suitable dyes and imaging agents include, but are not necessarily limited to, cytological or morphological dyes, immunological dyes such as immunohisto- and immunocyto-chemistry dyes, cytogenetical dyes, in situ hybridization dyes, cytochemical dyes, DNA and chromosome markers, and substrate binding assay dyes.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for removing any inherent autofluorescence associated with a biological material, comprising the steps of:
   a) acquiring a first reference image of the biological material;
   b) acquiring a first set of one or more images of the biological material using one or more filters corresponding to one or more information dyes;
   c) applying the one or more additional dyes to the biological material and then acquiring a second set of one or more images comprising a separate image of the biological material with each of the filters corresponding to the information dyes and a second reference image of the biological material;
   d) coregistering the first and second reference images;
   e) and then removing any inherent autofluorescence exhibited in the images acquired in steps c).

2. The method of claim 1, wherein the first and second reference images are acquired using a filter corresponding to a cyan fluorescent protein.

3. The method of claim 1, wherein step a) further comprises the step of, applying a reference dye, having a high signal to autofluorescence ratio, to the biological material and wherein the first and second reference images are acquired using a filter corresponding to the reference dye.

4. The method of claim 3, wherein the dye applied in step a) comprises a dye that corresponds to the UV spectrum.

5. The method of claim 4, wherein the dye applied in step a) corresponding to the UV spectrum is DAPI.

6. The method of claim 3, wherein the dye applied in step a) comprises a dye that corresponds to the IR spectrum.

7. The method of claim 1,
   wherein the first and second reference images of the biological material are acquired using a filter corresponding to a cyan fluorescent protein; and
   wherein the first reference image is a fixed image having a coordinate system and second reference image is a moving image having a coordinate system, and wherein the reference images are coregistered at least in part, to form a composite having a coordinate system, by estimating one or more underlying transformation parameters to map the moving image onto the fixed image coordinate system.

8. The method of claim 1,
   wherein step a) further comprises the step of, applying a reference dye, having a high signal to autofluorescence ratio, to the biological material;
   wherein the first and second reference images are acquired using a filter corresponding to the reference dye; and
   wherein the first reference image is a fixed image having a coordinate system and second reference image is a moving image having a coordinate system, and wherein the reference images are coregistered at least in part, to form a composite having a coordinate system, by estimating one or more underlying transformation parameters to map the moving image onto the fixed image coordinate system.

9. The method of claim 1, wherein the reference images are coregistered, at least in part, using a similarity transform that uses one or more transformation parameters selected from a group consisting of: translation, rotation and scaling.

10. The method of claim 1, wherein the reference images are coregistered by estimating one or more underlying transformation parameters to map a moving image onto a fixed image coordinate system, where;

$$\operatorname*{argmin}_{\theta} F(I_F(x_F, y_F), I_M(T(x_M, y_M; \theta))),$$

where F is the cost function, and T represents a spatial transformation with parameters $\theta$.

11. A system for removing inherent autofluorescence associated with a biological material, comprising:
   a) a processing device adapted to analyze a reference image of a biological material that exhibits the presence of one or more reference dyes, having a high signal to autofluorescence ratio;
   b) one or more filters corresponding to the reference dye and one or more filters corresponding to one or more information dyes;
   c) a digital imaging device adapted to acquire a first set of one or more images of the biological material, in conjunction with the filters corresponding to the reference dye and the one or more information dyes; and further adapted to acquire a second set of one or more images of the biological material, wherein the biological material further exhibits the presence of one or more of the information dyes, in conjunction with the filters corresponding to the reference dye and the one or more information dyes;
      wherein the second set of images comprises a separate image of the biological material with each of the filters corresponding to the reference dye and the one or more information dyes; and wherein the processing device is further adapted to coregister the reference images; and then remove the inherent autofluorescence, from the images exhibiting the presence of one or more of the information dyes.

12. The system of claim 11, wherein at least one of the reference dyes corresponds to the UV spectrum.

13. The system of claim 12, wherein at least one of the dyes that corresponds to the UV spectrum is DAPI.

14. The system of claim 11, wherein at least one of the reference dyes corresponds to the IR spectrum.

15. The system of claim 11,
wherein the digital imaging device is adapted to acquire a reference image of the biological material using a reference filter corresponding to a cyan fluorescent protein; and
wherein the processor is adapted to coregister the reference images by estimating one or more underlying transformation parameters to map the image coordinate system.

16. The system of claim 11, wherein the reference images are coregistered using an intensity-based or a featured based parameters.

17. The system of claim 11, wherein the reference images are coregistered, at least in part, using a similarity transform that incorporates translation, rotation, and scaling.

18. The system of claim 11 wherein the reference images are coregistered by estimating one or more underlying transformation parameters to map a moving image onto a fixed image coordinate system, where;

$$\underset{\theta}{\operatorname{argmin}} F(I_F(x_F, y_F), I_M(T(x_M, y_M; \theta))),$$

where F is the cost function, and T represents a spatial transformation with parameters $\theta$.

19. A system for removing inherent autofluorescence associated with a biological material, comprising:
a) a processing device adapted to analyze a reference image of a biological material taken using a reference filter corresponding to a cyan fluorescent protein, having a high signal to autofluorescence ratio;
b) one or more filters corresponding to one or more information dyes;
c) a digital imaging device adapted to acquire a first set of one or more images of the biological material, in conjunction with the reference filter and the filters corresponding to the one or more information dyes; and further adapted to acquire a second set of one or more images of the biological material, wherein the biological material further exhibits the presence of one or more of the information dyes, in conjunction with the reference filters and the filters corresponding to the one or more information dyes;
wherein the second set of images comprises a separate image of the biological material with the reference filter and with each of the filters corresponding to the one or more information dyes; and
wherein the processing device is further adapted to coregister the reference images; and then remove the inherent autofluorescence, from the images exhibiting the presence of one or more of the information dyes.

20. The system of claim 19, wherein the reference images are coregistered using an intensity-based or a featured based parameters.

21. The system of claim 19, wherein the reference images are coregistered, at least in part, using a similarity transform that incorporates translation, rotation, and scaling.

22. The system of claim 19 wherein the reference images are coregistered by estimating one or more underlying transformation parameters to map a moving image onto a fixed image coordinate system, where;

$$\underset{\theta}{\operatorname{argmin}} F(I_F(x_F, y_F), I_M(T(x_M, y_M; \theta))),$$

where F is the cost function, and T represents a spatial transformation with parameters $\theta$.

* * * * *